(12) United States Patent
Wyrick et al.

(10) Patent No.: US 6,410,243 B1
(45) Date of Patent: Jun. 25, 2002

(54) CHROMOSOME-WIDE ANALYSIS OF PROTEIN-DNA INTERACTIONS

(75) Inventors: John Wyrick, Cambridge; Richard A. Young, Weston; Bing Ren, Somerville; Francois Robert, Boston, all of MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 09/654,409

(22) Filed: Sep. 1, 2000

Related U.S. Application Data

(60) Provisional application No. 60/151,972, filed on Sep. 1, 1999.

(51) Int. Cl.$^7$ .................................................. C12Q 1/68
(52) U.S. Cl. ........................... 435/6; 435/7.1; 435/7.8; 435/91.1; 435/91.2; 435/320.1; 435/440; 364/496; 364/497; 364/578; 702/127; 702/30; 514/12; 514/44; 530/350; 536/24.1
(58) Field of Search ............................. 435/6, 7.1, 7.8, 435/91.1, 91.2, 320.1, 440; 364/496, 497, 578; 702/127, 30; 514/12, 44; 530/350; 536/24.1

(56) References Cited

U.S. PATENT DOCUMENTS

| | | | |
|---|---|---|---|
| 5,424,188 A | * | 6/1995 | Schneider et al. ............... 435/6 |
| 6,046,165 A | * | 4/2000 | Laughon et al. ............... 514/12 |
| 6,066,452 A | * | 5/2000 | Weissman et al. ............... 435/6 |
| 6,109,776 A | * | 8/2000 | Haas et al. ................... 364/496 |

OTHER PUBLICATIONS

Lipshutz et al. High Density Synthetic Oligonucleotide Arrays. Nature Genetics. vol. 21. Jan. 1999. pp. 20–24).*

Solomon, M.J., et al., "Mapping Protein–DNA Interactions in Vivo with Formaldehyde: Evidence That Histone H4 Is Retained on a Highly Transcribed Gene," *Cell* 53:937–947 (Jun. 17, 1988).

Solomon, M.J. and Varshavsky, A., "Formaldehyde–Mediated DNA–Protein Crosslinking: A Probe for In Vivo Chromatin Structures," *Proc. Natl. Sci. USA* 82:6470–6474 (Oct. 1985).

(List continued on next page.)

*Primary Examiner*—W. Gary Jones
*Assistant Examiner*—Janell E. Taylor
(74) *Attorney, Agent, or Firm*—Hamilton, Brook, Smith & Reynolds, P.C.

(57) ABSTRACT

The present invention relates to a method of identifying a region (one or more) of a genome of a cell to which a protein of interest binds. In the methods described herein, DNA binding protein of a cell is linked (e.g., covalently crosslinked) to genomic DNA of a cell. The genomic DNA to which the DNA binding protein is linked is removed and combined or contacted with DNA comprising a sequence complementary to genomic DNA of the cell under conditions in which hybridization between the identified genomic DNA and the sequence complementary to genomic DNA occurs. Region(s) of hybridization are region(s) of the genome of the cell to which the protein of binds.

11 Claims, 13 Drawing Sheets

(10 of 13 Drawing Sheet(s) Filed in Color)

OTHER PUBLICATIONS

Aparicio, O.M., et al., "Components and Dynamics of DNA Replication Complexes in S. cerevisiae: Redistribution of MCM Proteins and Cdc45p during S Phase," *Cell*, 91:59–69 (Oct. 3, 1997).

Tanaka, T., et al., "Loading of an Mcm Protein onto DNA Replication Origins Is Regulated by Cdc6p and CDKs," *Cell*, 90:649–660 (Aug. 22, 1997).

Holstege, F.C.P., et al., "Dissecting the Regulatory Circuitry of a Eukaryotic Genome," *Cell*, 95:717–728 (Nov. 25, 1998).

Chee, M., et al., "Accessing Genetic Information with High–Density DNA Arrays," *Science*, 274:610–614 (Oct. 25, 1996).

DeRisi, J.L., et al., "Exploring the Metabolic and Genetic Control of Gene Expression on a Genomic Scale," *Science*, 278:680–686 (Oct. 24, 1997).

Orlando, V., "Mapping Chomosomal Proteins in vivo by Formaldehyde–Crosslinked–Chromatin Innuoprecipitation," *TIBS*, 25:99–104 (Mar. 2000).

Roberts, C.J., "Signaling and Circuitry of Multiple MAPK Pathways Revealed by a Matrix of Global Gene Expression Profiles," *Science 287*: 873–880 (Feb. 4, 2000).

Hecht, A., et al., "Spreading of Transcriptional Repressor SIR3 From Telomeric Heterochomatin," *Nature 383*:92–96 (Sep. 5, 1996).

Blat, Y., et al., "Cohesins Bind to Preferential Sites along Yeast Chromosome III, with Differential Regulation along Arms versus the Centric Region," *Cell 98*:249–259 (Jul. 23, 1999).

Ren, B., et al., "Genome–Wide Location and Function of DNA Binding Proteins," *Science 290*: 2306–2309 (Dec. 22, 2000).

* cited by examiner

| Binding | | | Binding | | | | Expression | |
|---|---|---|---|---|---|---|---|---|
| Glucose | Galactose | Expression (Gal/Glu) | | Glucose | | Galactose | | Ratio | |
| | | | Name | Ratio | p-value | Ratio | p-value | Gal/Glu | Description |
| | | | GAL2 | 2.8 | 2.5X10-02 | 9.5 | 1.5X10-10 | 188.6 | Galactose permease |
| | | | GAL3 | 1.4 | 5.4X10-01 | 8.2 | 3.5X10-10 | 18.2 | Regulatory protein required for rapid induction of galactose pathway |
| | | | GAL7 | 0.4 | 2.0X10+00 | 8.2 | 6.4X10-10 | 170.1 | UDP-glucose–hexose-1-phosphate uridylyltransferase |
| | | | GAL1 | 1.3 | 6.0X10-01 | 7.8 | 1.5X10-09 | 271.3 | Galactokinase, first step in galactose metabolism |
| | | | GAL10 | 1.3 | 6.0X10-01 | 7.8 | 1.5X10-09 | 118.8 | UDP-glucose 4-epimerase |
| | | | FUR4 | 0.3 | 2.0X10+00 | 4.6 | 4.3X10-08 | 4.6 | Uracil permease (adjacent to GAL1) |
| | | | GCY1 | 0.9 | 1.2X10+00 | 4.3 | 1.3X10-07 | 93.1 | Galactose-induced oxidoreductase |
| | | | MTH1 | 0.9 | 1.2X10+00 | 4.0 | 2.4X10-07 | 21.6 | Repressor of hexose transport genes |
| | | | GAL80 | 0.5 | 1.3X10+00 | 3.7 | 7.0X10-07 | 4.0 | Negative regulator for expression of galactose-induced genes |
| | | | PCL10 | 0.6 | 1.8X10+00 | 3.0 | 6.8X10-06 | 2.6 | Cyclin that associates with Pho85p, involved in glycogen accumulation |
| | | | YBR022W | 3.7 | 1.7X10-02 | 10.4 | 1.2X10-10 | 1.5 | Unknown function (adjacent to GAL1) |
| | | | YDR008C | 1.4 | 5.5X10-01 | 8.2 | 3.5X10-10 | 1.5 | Unknown function (share intergenic region with GAL3) |
| | | | GIS3 | 2.7 | 2.9X10-02 | 8.0 | 4.8X10-10 | 1.0 | Multicopy suppressor of the Gal(-) phenotype of snf1 mig1 srb8/10/11 cells |
| | | | TLC1 | 0.6 | 1.9X10+00 | 4.2 | 1.2X10-07 | 1.0 | RNA subunit of telomerase |
| | | | PDX3 | 0.6 | 1.9X10+00 | 4.2 | 1.2X10-07 | 1.6 | Pyridoxine phosphate oxidase |
| | | | RIO1 | 0.9 | 1.2X10+00 | 4.3 | 1.3X10-07 | 1.4 | Unknown function (share intergenic region with GCY1) |
| | | | YJR044C | 2.3 | 6.6X10-02 | 4.0 | 3.4X10-07 | 1.7 | Unknown function |
| | | | SNQ2 | 0.9 | 1.1X10+00 | 3.5 | 1.1X10-06 | 0.6 | Drug-efflux pump involved in resistance to multiple drugs (adjacent to GAL3) |
| | | | YDR010C | 0.9 | 1.1X10+00 | 3.5 | 1.1X10-06 | 1.0 | Unknown function (adjacent to GAL3) |
| | | | APC9 | 1.9 | 1.9X10-01 | 3.6 | 2.0X10-06 | 1.2 | Component of the anaphase-promoting complex (APC) |
| | | | CSG2 | 0.5 | 1.9X10+00 | 3.3 | 2.4X10-06 | 1.3 | Required for synthesis of the mannosylated sphingolipids |
| | | | RPL4B | 0.9 | 1.3X10+00 | 3.3 | 2.8X10-06 | 0.8 | Ribosomal protein L4, Gene (adjacent to GAL3) |
| | | | YGL132W | 0.6 | 1.8X10+00 | 3.0 | 9.1X10-06 | 1.0 | Unknown function, (adjacent to PCL10) |
| | | | CHA4 | 1.5 | 4.1X10-01 | 3.1 | 9.8X10-06 | 1.0 | Zinc-finger protein required for transcriptional activation of CHA1 |

CHROMOSOME-WIDE ANALYSIS OF PROTEIN-DNA INTERACTIONS

RELATED APPLICATIONS

This application claims the benefit of U.S. Application No. 60/151,972, filed on Sep. 1, 1999, the entire teachings of which are incorporated herein by reference.

BACKGROUND OF THE INVENTION

Many proteins involved in regulating genome expression, chromosomal replication and cellular proliferation function through their ability to bind specific sites in the genome. Transcriptional activators, for example, bind to specific promoter sequences and recruit chromatin modifying complexes and the transcription apparatus to initiate RNA synthesis. The remodeling of gene expression that occurs as cells move through the cell cycle, or when cells sense changes in their environment, is effected in part by changes in the DNA-binding status of transcriptional activators. Distinct DNA-binding proteins are also associated with centromeres, telomeres, and origins of DNA replication, where they regulate chromosome replication and maintenance. Although considerable knowledge of many fundamental aspects of gene expression and DNA replication has been obtained from studies of DNA-binding proteins, an understanding of these proteins and their functions is limited by our knowledge of their binding sites in the genome.

Proteins which bind to a particular region of DNA can be detected using known methods. However, a need exists for a method which allows examination of the binding of proteins to DNA across the entire genome of an organism.

SUMMARY OF THE INVENTION

The present invention relates to a method of identifying a region (one or more) of a genome of a cell to which a protein of interest binds. In the methods described herein, DNA binding protein of a cell is linked (e.g., covalently crosslinked) to genomic DNA of a cell. The genomic DNA to which the DNA binding protein is linked is identified and combined or contacted with DNA comprising a sequence complementary to genomic DNA of the cell (e.g., all or a portion of a cell's genomic DNA such as one or more chromosome or chromosome region) under conditions in which hybridization between the identified genomic DNA and the sequence complementary to genomic DNA occurs. Region(s) of hybridization are region(s) of the genome of the cell to which the protein of interest binds. The methods of the present invention are preferably performed using living cells.

In one embodiment, proteins which bind DNA in a cell are crosslinked to the cellular DNA. The resulting mixture, which includes DNA bound by protein and DNA which is not bound by protein is subject to shearing conditions. As a result, DNA fragments of the genome crosslinked to DNA binding protein are generated and the DNA fragment (one or more) to which the protein of interest is bound is removed from the mixture. The resulting DNA fragment is then separated from the protein of interest and amplified, using known methods. The DNA fragment is combined with DNA comprising a sequence complementary to genomic DNA of the cell, under conditions in which hybridization between the DNA fragment and a region of the sequence complementary to genomic DNA occurs; and the region of the sequence complementary to genomic DNA to which the DNA fragment hybridizes is identified. The identified region (one or more) is a region of the genome of the cell, such as a selected chromosome or chromosomes, to which the protein of interest binds.

In a particular embodiment, the present invention relates to a method of identifying a region of a genome (such as a region of a chromosome) of a cell to which a protein of interest binds, wherein the DNA binding protein of the cell is crosslinked to genomic DNA of the cell using formaldehyde. DNA fragments of the crosslinked genome are generated and the DNA fragment to which the protein of interest is bound is removed or separated from the mixture, such as through immunoprecipitation using an antibody that specifically binds the protein of interest. This results in separation of the DNA-protein complex. The DNA fragment in the complex is separated from the protein of interest, for example, by subjecting the complex to conditions which reverse the crosslinks. The separated DNA fragment is amplified using ligation-mediated polymerase chain reaction (LM-PCR), and then fluorescently labeled. The labeled DNA fragment is contacted with a DNA microarray comprising a sequence complementary to genomic DNA of the cell, under conditions in which hybridization between the DNA fragment and a region of the sequence complementary to genomic DNA occurs. The region of the sequence complementary to genomic DNA to which the DNA fragment hybridizes is identified by measuring fluorescence intensity, and the fluorescence intensity of the region of the sequence complementary to genomic DNA to which the DNA fragment hybridizes is compared to the fluorescence intensity of a control. Fluorescence intensity in a region of the sequence complementary to genomic DNA which is greater than the fluorescence intensity of the control in that region of the sequence complementary to genomic DNA marks the region of the genome in the cell to which the protein of interest binds.

Also encompassed by the present invention is a method of determining a function of a protein of interest which binds to the genomic DNA of a cell. In this method, DNA binding protein of the cell is crosslinked to the genomic DNA of the cell. DNA fragments of the genome crosslinked to DNA binding protein are then generated, as described above, and the DNA fragment (one or more) to which the protein of interest is bound is removed from the mixture. The resulting DNA fragment is then separated from the protein of interest and amplified. The DNA fragment is combined with DNA comprising a sequence complementary to genomic DNA of the cell, under conditions in which hybridization between the DNA fragment and a region of the sequence complementary to genomic DNA occurs; and the region of the sequence complementary to genomic DNA to which the DNA fragment hybridizes is identified. This identified region is a region of the genome of the cell to which the protein of interest binds. The identified region is characterized and the characteristic of the identified region indicates the function of the protein of interest (e.g., a regulatory protein such as a transcription factor; an oncoprotein).

The present invention also relates to a method of determining whether a protein of interest which binds to genomic DNA of a cell functions as a transcription factor. In one embodiment, DNA binding protein of the cell is crosslinked to the genomic DNA of the cell. DNA fragments of the crosslinked genome are generated and the DNA fragment to which the protein of interest is bound is removed from the mixture. The resulting DNA fragment is separated from the protein of interest and amplified. The DNA fragment is combined with DNA comprising a sequence complementary to genomic DNA of the cell, under conditions in which hybridization between the DNA fragment and a region of the sequence complementary to genomic DNA occurs. The region of the sequence complementary to genomic DNA to which the DNA fragments hybridizes is identified; wherein if the region of the genome is a regulatory region, then the protein of interest is a transcription factor.

The methods described herein facilitate the dissection of the cells regulatory network of gene expression across the entire genome and aid in the identification of gene function.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 6A shows the set of 24 genes whose promoter regions are most likely to be bound by Gal4 by the analysis criteria described herein.

DETAILED DESCRIPTION OF THE INVENTION

Figure 1:
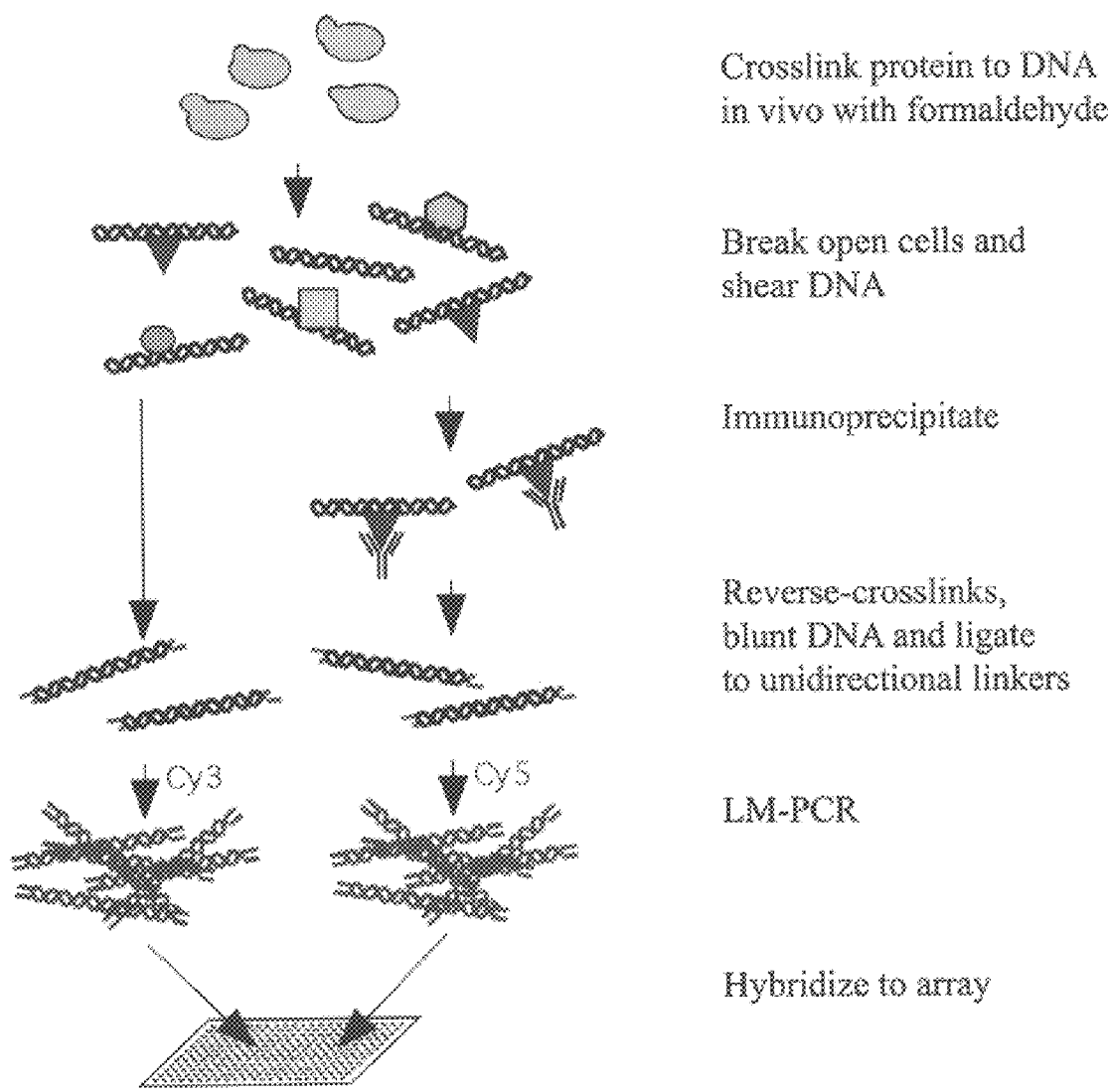
FIG. 1 is an illustration of the Genome-wide Monitoring Protein-DNA interactions described herein.

Understanding how DNA-binding proteins control global gene expression, chromosomal replication and cellular proliferation would be facilitated by identification of the chromosomal locations at which these proteins function in vivo.

Described herein is a genome-wide location profiling method for DNA-bound proteins, which has been used to monitor dynamic binding of gene-specific transcription factors and components of the general transcription apparatus in yeast cells. The genome-wide location method correctly identified known sites of action for the transcriptional activators Gal4 and Ste12 and revealed unexpected functions for these activators. The combination of expression and location profiles identified the global set of genes whose expression is under the direct control of specific activators and components of the transcription apparatus as cells responded to changes in their extracellular environment. Genome-wide location analysis provides a powerful tool for further dissecting gene regulatory networks, annotating gene functions and exploring how genomes are replicated.

Accordingly, the present invention provides methods of examining the binding of proteins to DNA across the genome (e.g., the entire genome or a portion thereof, such as one or more chromosomes or a chromosome regions) of an organism. In particular, the present invention relates to a method of identifying a region (one or more) of genomic DNA of a cell to which a protein of interest binds. In one embodiment, proteins which bind DNA in a cell are crosslinked to the cellular DNA. The resulting mixture, which includes DNA bound by protein and DNA which is not bound by protein is subject to shearing conditions. As a result, DNA fragments of the genome crosslinked to DNA binding protein are generated and the DNA fragment (one or more) to which the protein of interest is bound is removed from the mixture. The resulting DNA fragments are then separated from the protein of interest and amplified using known techniques. The DNA fragment is then combined with DNA comprising a sequence complementary to genomic DNA of the cell, under conditions in which hybridization between the DNA fragments and the sequence complementary to genomic DNA occurs; and the region of the sequence complementary to genomic DNA to which the DNA fragment hybridizes is identified. The identified region is a region of the genome of the cell to which the protein of interest binds.

Also encompassed by the present invention is a method of determining a function of a protein of interest which binds to the genomic DNA of a cell. In this method, DNA binding protein of the cell is crosslinked to the genomic DNA of the cell. DNA fragments of the genome crosslinked to DNA binding protein are then generated, as described above, and the DNA fragment (one or more) to which the protein of interest is bound is removed. The resulting DNA fragment is then separated from the protein of interest and amplified. The DNA fragment is then combined with DNA comprising a sequence complementary to genomic DNA of the cell, under conditions in which hybridization between the DNA fragment and a region of the sequence complementary to genomic DNA occurs; and the region of the sequence complementary to genomic DNA to which the DNA fragment hybridizes is identified and is a region of the genome of the cell to which the protein of interest binds. The identified region is characterized (e.g., a regulatory region) and the characteristic of the identified region indicates a function of the protein of interest (e.g., a transcription factor; an oncoprotein).

The present invention also relates to a method of determining whether a protein of interest which binds to genomic DNA of a cell functions as a transcription factor. In one embodiment, DNA binding protein of the cell is crosslinked to genomic DNA of the cell and DNA fragments of the crosslinked genome are generated. The DNA fragment to which the protein of interest is bound are removed. The resulting DNA fragment is separated from the protein of interest and amplified. The DNA fragment is combined with DNA comprising a sequence complementary to genomic DNA of the cell, under conditions in which hybridization between the DNA fragments and sequence complementary to genomic DNA occurs. The region of the sequence complementary to genomic DNA to which the DNA fragments hybridizes is identified wherein if the region of the genome is a regulatory region, then the protein of interest is a transcription factor.

The methods of the present invention can be used to examine and/or identify DNA binding of proteins across the entire genome of a eukaryotic organism. For example, DNA binding proteins across the entire genome of eukaryotic organisms such as yeast, Drosophila and humans can be analyzed. Alternatively, they can be used to examine and/or identify DNA binding of proteins to an entire chromosome or set of chromosomes of interest.

A variety of proteins which bind to DNA can be analyzed. For example, any protein involved in DNA replication such as a transcription factor, or an oncoprotein can be examined in the methods of the present invention.

There are a variety of methods which can be used to link DNA binding protein of the cell to the genome of the cell. For example, UV light can be used. In a particular embodiment, formaldehyde is used to crosslink DNA binding proteins to the genomic DNA of a cell.

In the methods of the present invention, identification of DNA fragments bound to the protein of interest can be removed from the mixture comprising DNA fragment(s) bound to the protein of interest and DNA fragments which are not bound to the protein of interest, using a variety of methods. For example, immunoprecipitation using an antibody (e.g., polyclonal, monoclonal) or antigen binding fragment thereof which binds (specifically) to the protein of interest, can be used. In addition, the protein of interest can be labeled or tagged using, for example, an antibody epitope (e.g., hemagglutinin (HA)).

The DNA fragments in the methods described herein can be amplified using, for example, ligation-mediated polymerase chain reaction (e.g., see *Current Protocols in Molecular Biology*, Ausubel, F. M. et al., eds. 1991, the teachings of which are incorporated herein by reference).

The DNA comprising the complement sequence of the genome of the cell can be combined with the isolated DNA fragment to which the protein of interest binds using a variety of methods. For example, the complement sequence can be immobilized on a glass slide (e.g., Corning Microarray Technology (CMT™) GAPS™) or on a microchip. Conditions of hybridization used in the methods of the present invention include, for example, high stringency conditions and/or moderate stringency conditions. See e.g., pages 2.10.1–2.10.16 (see particularly 2.10.8–11 ) and pages 6.3.1–6 in *Current Protocols in Molecular Biology*). Factors such as probe length, base composition, percent mismatch between the hybridizing sequences, temperature and ionic strength influence the stability of hybridization. Thus, high or moderate stringency conditions can be determined empirically, and depend in part upon the characteristics of the known nucleic acids (DNA, RNA) and the other nucleic acids to be assessed for hybridization thereto.

The methods of the present invention can further comprise comparing the results to a control. For example, in one embodiment, the methods of the present invention can be carried out using a control protein which is not a DNA binding protein. In one embodiment, immunoprecipitation is performed using an antibody against an HA or MYC epitope tag. The results of immunoprecipitating the protein of interest containing the tag, and the protein of interest without the tag are compared. The untagged protein should not be immunoprecipitated, and thus, serves as a negative control.

As described in the exemplification, a particular embodiment of the present invention comprises the combined use of Chromatin Immunoprecipitation (ChIP) and Genome-wide expression monitoring micro arrays. Chromatin immunoprecipitation allows the detection of proteins that are bound to a particular region of DNA. It involves four steps: (1) formaldehyde cross-linking proteins to DNA in living cells, (2) disrupting and then sonicating the cells to yield small fragments of cross-linked DNA, (3) immunoprecipitating the protein-DNA crosslinks using an antibody which specifically binds the protein of interest, and (4) reversing the crosslinks and amplifying the DNA region of interest using the Polymerase Chain Reaction (PCR). Analysis of the PCR product yield compared to a non-immunoprecipitated control determines whether the protein of interest binds to the DNA region tested. However, each region of DNA must be tested individually by PCR. Thus, the ChIP technique is limited to the small set of DNA regions that are chosen to be tested.

In contrast, the present method is not limited to amplifying individual DNA regions by performing PCR with specific primers. Rather the entire genome is amplified using a Ligation-mediated PCR (LMPCR) strategy. The amplified DNA was fluorescently labeled by including fluorescently-tagged nucleotides in the LM-PCR reaction. Finally, the labeled DNA was hybridized to a DNA microarray containing spots representing all or a subset (e.g., a chromosome or chromosomes) of the genome. The fluorescent intensity of each spot on the microarray relative to a non-immunoprecipitated control demonstrated whether the protein of interest bound to the DNA region located at that particular spot. Hence, the methods described herein allow the detection of protein-DNA interactions across the entire genome.

In particular, DNA microarrays consisting of most of yeast chromosome III plus approximately 15 model genes whose expression have been well studied were constructed. These arrays were used in conjunction with the ChIP technique to study the DNA-binding properties of transcription factors and the transcription apparatus genome-wide. The methods described herein provide insights into the mechanism and regulation of gene expression in eukaryotic cells.

The genome-wide location analysis method described herein allows protein-DNA interactions to be monitored across the entire yeast genome and is diagramed in FIG. 1. The method combines a modified Chromatin Inmunoprecipitation (ChIP) procedure, which has been previously used to study in vivo protein-DNA interactions at one or a small number of specific DNA sites, with DNA microarray analysis. Briefly, cells are fixed with formaldehyde, harvested by sonication, and DNA fragments that are crosslinked to a protein of interest are enriched by immunoprecipitation with a specific antibody. After reversal of the crosslinking, the enriched DNA is amplified and labeled with a fluorescent dye using ligation-mediated PCR (LM-PCR). A sample of DNA that has not been enriched by immunoprecipitation is subjected to LM-PCR in the presence of a different fluorophore, and both IP-enriched and unenriched pools of labeled-DNA are hybridized to a single DNA microarray containing all yeast intergenic sequences. The IP-enriched/unenriched ratio of fluorescence intensity obtained from three independent experiments can be used with a weighted average analysis method to calculate the relative binding of the protein of interest to each sequence represented on the array (see FIG. 2).

Figure 5A:
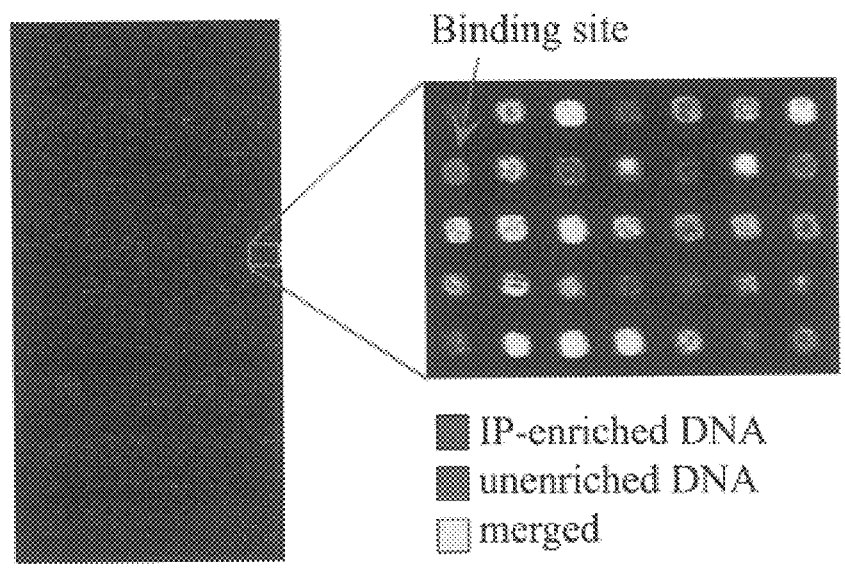
FIG. 5A is an example of a scanned image. The unenriched and IP enriched DNA generates green fluorescence and red fluorescence respectively. The close-up image shows examples of spots for which the red intensity is over-represented, indicating binding of the targeted protein to these DNA sequences.
Figure 5B:
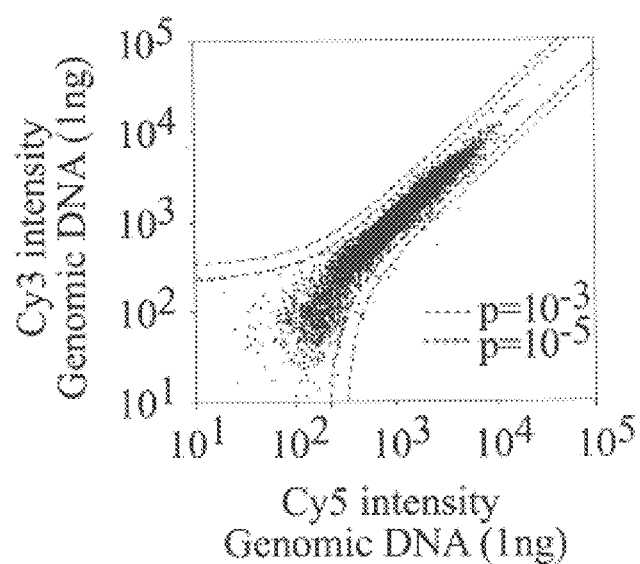
FIG. 5B shows that small amounts of DNA can be quantitatively amplified and labeled with Cy3 and CY5 fluorophores. Cy3- and Cy5-labeled DNA from 1 ng of yeast genomic DNA was prepared using the LM-PCR method described in the text. The resulting DNA samples were mixed and hybridized to a yeast intragenic DNA microarray. Low intensity spots have larger variations than high intensity spots, probably due to background noise.

Four features of the global location profiling method were found to be critical for consistent, high-quality results. First, DNA microarrays with consistent spot quality and even signal background play an obvious role. An example of an image generated by the technique described herein is shown in FIG. 5A. Second, the LM-PCR method described herein was developed to permit reproducible amplification of very small amounts of DNA; signals for greater than 99.9% of genes were essentially identical within the error range when independent samples of 1 ng of genomic DNA were amplified with the LM-PCR method (FIG. 5B). Third, each experiment was carried out in triplicate, allowing an assessment of the reproducibility of the binding data. And fourth, a single-array error model described by Hughs et al, (2000) was adopted to handle noise associated with low intensity spots and to average repeated experiments with appropriate weights.

The quantitative amplification of small amount of DNA generates some uncertainty for the low intensity spots. In order to track that uncertainty and to be able to average repeated experiments with appropriate related weights, we adopted an single-array error model that was first described by Hughs et al, (2000). According to this error model, the significance of a measured ratio at a spot is defined by a statistic X, which takes the form $$X=(a_2-a_1)/[\sigma_1^2+\sigma_2^2+f^2(a_1^2+a_2^2)]^{1/2} \quad (1)$$

where $a_{1,2}$ are the intensities measured in the two channels for each spot, $\sigma_{1,2}$ are the uncertainties due to background subtraction, and f is a fractional multiplicative error such as would come from hybridization non-uniformities, fluctuations in the dye incorporation efficiency, scanner gain fluctuations, ets. X is approximately normal. The parameters σ and f were chosen such that X has unit variance. The significance of a change of magnitude |x| is then calculated as $$p=2x(1-Erf(|X|)). \quad (2)$$

While this invention has been particularly shown and described with references to preferred embodiments thereof, it will be understood by those skilled in the art that various changes in form and details may be made therein without departing from the scope of the invention encompassed by the appended claims.

EXEMPLIFICATION

Example 1

Design of Yeast Chromosome III and Selected Model Genes Array for the Characterization of Protein-DNA Interactions Array contains all non-overlapping open reading frames (ORF) on Chromosome III (See the Table). When a sequence contains part or all of two potential reading frames, the larger sequence was chosen to represent the ORF. Any remaining sequence was included in intergenic fragments.

All intergenic regions larger than 100 bp are represented by fragments averaging 500 bp. Where regions are greater than 700 bp, they are broken into multiple fragments of 300 to 600 bps. PCR primers for each region were chosen using the Saccharomyces Genomic Database (SGD) "Design Primers" program from Stanford University. The total number of intergenic fragments equals 241 for Chromosome III.

The location and size of open reading frames were determined from the Saccharomyces Genomic Database (SGD) functional chromosomal map.

An additional 17 model genes (see the Table) were selected based on their high frequency of citation in transcription literature. Each gene was amplified as well as 1–2 kb upstream and 500 bp downstream of the coding region.

ChIP—Microarray Protocols

PCR generation of unmodified yeast ORF DNA
100 μl reaction generally yields approximately 5–6 μg DNA
RXN mix:
10.0 μl 10×PCR buffer (Perkin Elmer, AmpliTaq)
8.0 μl 25 mM MgCl2 (Perkin Elmer, AmpliTaq)
10.0 μl 10×dNTPs (2 mM each, Pharmacia 100 mM stocks)
1.0–2.0 μl ORF DNA (Research Genetics, approximately 10 ng)
2.5 μl each universal primer (Research Genetics, 20 μM solution)
1.6 μl diluted Pfu DNA polymerase (diluted 1:100 in water, Strategene, 0.02 U)
1.0 μl AmpliTaq DNA polymerase (5 U, Perkin Elmer)
63.4 μl ddH$_2$O PCR Generation of Yeast Intergenic regions
100 μl reaction generally yields approximately 5–6 ug DNA
RXN mix:
10.0 μl 10×PCR buffer (Perkin Elmer, AmpliTaq)
8.0 μl 25 mM MgCl2 (Perkin Elmer, AmpliTaq)
10.0 μl 10×dNTPs (2 mM each, Pharmacia 100 mM stocks)
1.0 μl Yeast Genomic DNA (Research Genetics, approximately 100 ng)
5.0 μl each primer (Research Genetics, 20 μM solution)
1.6 μl diluted Pfu DNA polymerase (diluted 1:100 in water, Strategene 0.02 U)
1.0 μl AmpliTaq DNA polymerase (5 U, Perkin Elmer)
58.4 μl ddH$_2$O Cycling for ORF and intergenic DNA
95° C. 3 min
30 cycles of:
94° C. 30 sec
60° C. 30 sec
72° C. 2 min PCR Cleanup:
Reactions were cleaned by Qiagen QIAquick 96 PCR purification kits according to the manufacturers' protocol with the following exception. DNA was eluted with 120 μl of T.E. 8.0 (10 mm Tris, 1 mm EDTA, pH8.0). T.E. 8.0 was applied to the Qiagen membrane and allowed to sit 5 minutes before elution. The DNA was collected into a Corning polypropylene 96 well plate.

Reactions were quantified by visualizing 1 μl of the purified DNA on an agarose gel compared to a known quantity of lambda DNA cut with HindIII (Promega).

DNA was stored at −20 until shortly before printing. The DNA was then dried down by speed vac in the Corning microtiter plates to less than 5 μl.

Printing
PCR reactions were resuspended to approximately 0.5 mg/ml in 3×SSC. SSC was made as a 20×stock (3M NaCl, 0.3M Na$_3$citrate.2H$_2$O, pH'd to 7.0 with HCl) and diluted to the desired concentration with H$_2$O.

10–15 μl of the DNA was placed in a Corning 96 or 384 well plate and GAPS coated slides were printed using the Cartessian Robot. PCR products should be greater than 250 pb.

Slide Processing
1. Rehydrated arrays by holding slides over a dish of hot ddH$_2$O (~10 sec).
2. Snap-dried each array (DNA side up) on a 100° C. hot plate for ~3 seconds.
3. UV X-linked DNA to the glass by using a Stratalinker set for 60 mJoules.
4. Dissolved 5 g of succinic anhybride (Aldrich) in 315 mL of n-methyl-pyrrilidinone.
5. To this, added 35 mL of 0.2M NaBorate pH 8.0, and stirred until dissolved (Boric Acid pH'd with NaOH).
6. Soaked arrays in this solution for 15 minutes with shaking.
7. Transferred arrays to 95° C. water bath for 2 minutes.
8. Quickly transferred arrays to 95% EtOH for 1 minute.
9. Air dried slides array side up at a slight angle (close to vertical).

Slide Pre-hybridization
1. Incubated slide in 3.5×SSC, 0.1% SDS, 10 mg/ml BSA (Sigma) in a Coplin jar for 20 minutes at 50° C. (Place Coplin jar in water bath).
2. Washed slide by dipping in water and then isopropanol.
3. Air dried array side up at slight angle (close to vertical).

Probe Preparation
1. The probe volume should be 20–30 μl for a small coverslip (25 mm$^2$) and 40–60 μl for a large cover slip (24×60 mm).
2. Brought probe (cDNA or PCR based) up to final hyb volume in 3×SSC, 0.1% SDS with 10 μg E. coli tRNA (Boehringer-Mannheim).
3. Boiled in heat block for 3–5 minutes.
4. Snaped cool on ice. And spun.

Hybridization
1. Pipetted probe onto slide. Dropped cover slip onto liquid avoiding bubbles.
2. Assembled over 50° C. waterbath in hybridization chamber. Clamped shut.
3. Submerged in 50° C. waterbath overnight.

Scanning
1. Dissambled hybridization right side up.
2. Removed coverslip with fingers or tweezers.
3. Placed in 0.1×SSC, 0.1% SDS at room temperature for 5–10 minutes.
4. Transfered slides to 0.1×SSC for 2.5 minutes and again for 2.5 minutes.
5. Blew dry and scan slide.

Data Analysis
The data generated from scanning was analyzed using the ImaGene software.

THE TABLE

| Yeast ORF | Model Genes | | |
|---|---|---|---|
| YCL001w | RER1 | YOL086c | ADH1 |
| YCL001w-a | | YBR115c | LYS2 |
| YCL002c | | YBR039c | PHO5 |
| YCL004w | PGS1 | YIR019c | FLO11 |
| YCL005w | | YDL215c | GDH2 |
| YCL006c | | YER103w | SSA4 |
| YCL007c | CWH36 | YHR053c | CUP1 |
| YCL008c | STP22 | YKL178c | STE3 |
| YCL009c | ILV6 | YIL163c | SUC2 |
| YCL010c | | YOR202w | HIS3 |
| YCL011c | GBP2 | YJR048w | CYC1 |
| YCL012w | | YJR153c | INO1 |
| YCL014w | BUD3 | YBR020w | GAL1 |
| YCL016c | | YBR019c | GAL10 |
| YCL017c | NSF1 | YDL227c | HO |

THE TABLE-continued

| Yeast ORF | Model Genes | | |
|---|---|---|---|
| YCL018w | LEU2 | YPL256c | CLN2 |
| YCL019w | | YGR108w | CLB1 |
| YCL020w | | | |
| YCL024w | | | |
| YCL025c | AGP1 | | |
| YCL026ca | FRM2 | | |
| YCL027w | FUS1 | | |
| YCL028w | | | |
| YCL029w | BIK1 | | |
| YCL030c | HIS4 | | |
| YCL031c | RPB7 | | |
| YCL032w | STE50 | | |
| YCL033c | | | |
| YCL034w | | | |
| YCL035c | | | |
| YCL036w | | | |
| YCL037c | SRO9 | | |
| YCL038c | | | |
| YCL039w | | | |
| YCL040w | GLK1 | | |
| YCL041c | | | |
| YCL042w | | | |
| YCL043c | PDI1 | | |
| YCL044c | | | |
| YCL045c | | | |
| YCL046w | | | |
| YCL047c | | | |
| YCL048w | | | |
| YCL049c | | | |
| YCL050c | APA1 | | |
| YCL051w | LRE1 | | |
| YCL052c | PBN1 | | |
| YCL054w | | | |
| YCL055w | KAR4 | | |
| YCL056w | | | |
| YCL057w | PRD1 | | |
| YCL058c | | | |
| YCL059c | KRR1 | | |
| YCL061c | | | |
| YCL063w | | | |
| YCL064c | CHA1 | | |
| YCL065w | | | |
| YCL066w | HMLALPHA1 | | |
| YCL067c | HMLALPHA2 | | |
| YCL068c | | | |
| YCL069w | | | |
| YCL073c | | | |
| YCL074w | | | |
| YCL075w | | | |
| YCL076w | | | |
| YCR001W | | | |
| YYCR002c | CDC10 | | |
| YCR003w | MRPL32 | | |
| YCR004c | YCP4 | | |
| YCR005c | CIT2 | | |
| YCR006c | | | |
| YCR007c | | | |
| YCR008w | SAT4 | | |
| YCR009c | RVS161 | | |
| YCR010c | | | |
| YCR011c | ADP1 | | |
| YCR012w | PGK1 | | |
| YCR014c | POL4 | | |
| YCR015c | | | |
| YCR016w | | | |
| YCR017c | | | |
| YCR018c | SRD1 | | |
| YCR018ca | | | |
| YCR019w | | | |
| YCR020c | PET18 | | |
| YCR020CA | MAK31 | | |
| YCR020wb | HTL1 | | |
| YCR021c | HSP30 | | |
| YCR022c | | | |
| YCR023c | | | |
| YCR024c | | | |
| YCR024CA | PMP1 | | |

THE TABLE-continued

Figure 2:
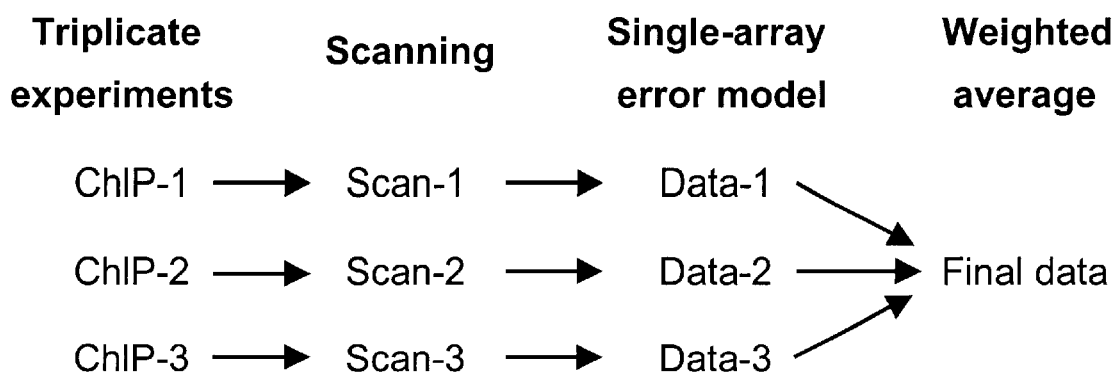
FIG. 2 shows how the relative binding of the protein of interest to each sequence represented on an array was calculated using a weighted average analysis.
Figure 3:
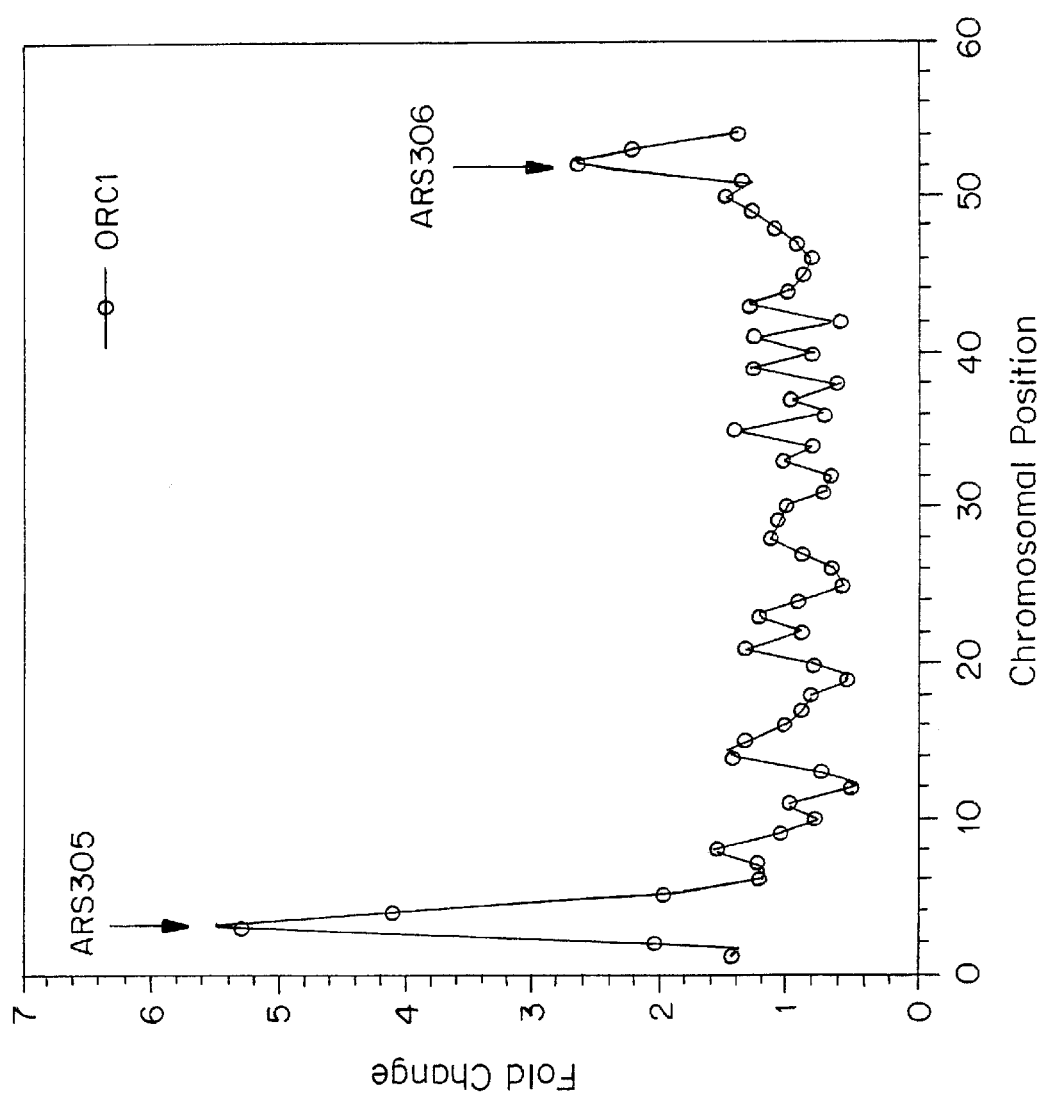
FIG. 3 is a graph of chromosomal position versus fold change of Genome-wide Monitoring Protein-DNA interactions.
Figure 4:
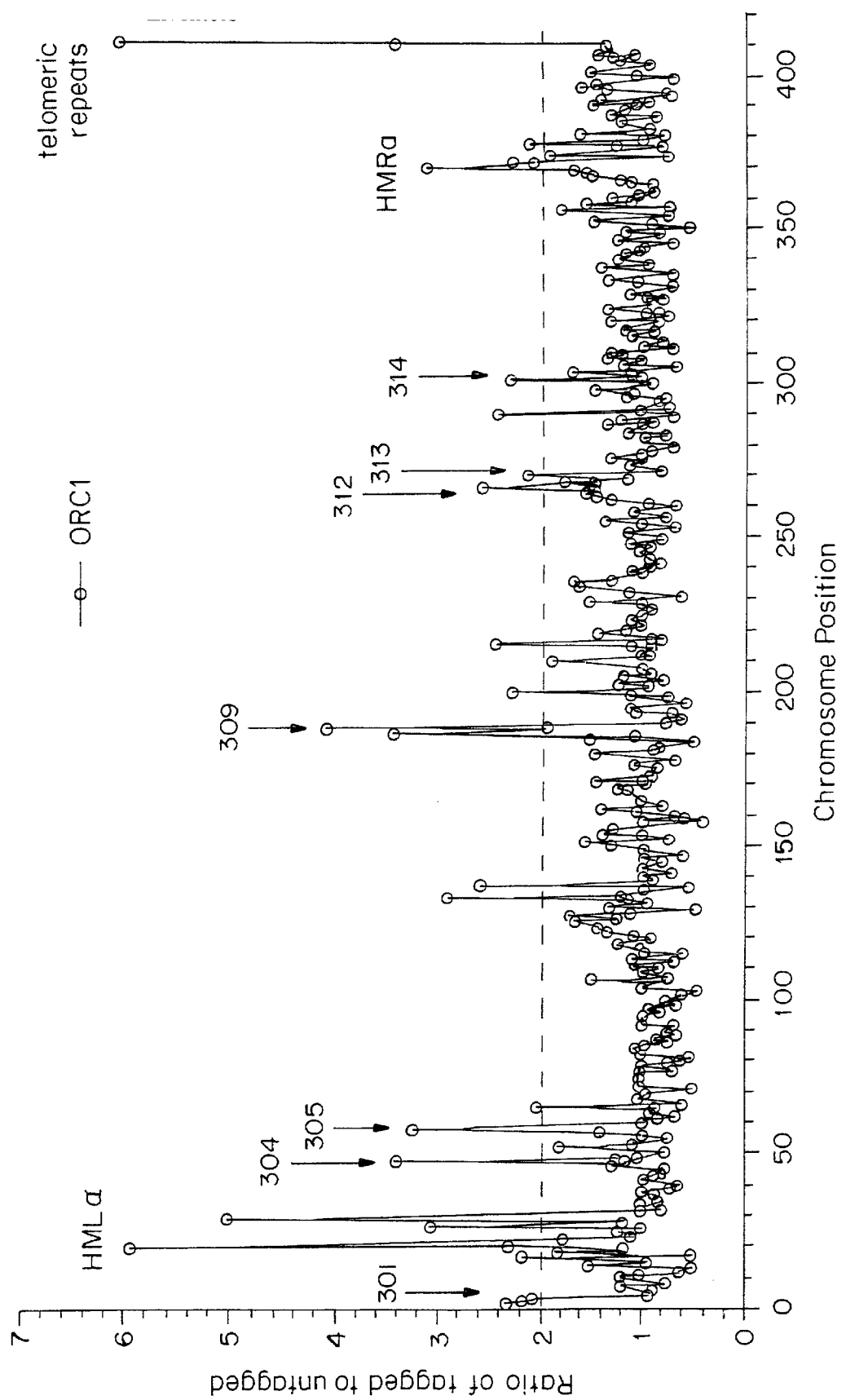
FIG. 4 is a graph of chromosome position versus ratio of tagged to untagged for binding ORC1 to yeast chromosome III.

| Yeast ORF | Model Genes |
|---|---|
| YCR025c | |
| YCR026c | |
| YCR027c | |
| YCR028c | FEN2 |
| YCR028CA | RIM1 |
| YCR030c | |
| YCR031c | RPS14A |
| YCR032w | BPH1 |
| YCR033w | |
| YCR034w | FEN1 |
| YCR035c | RRP43 |
| YCR036w | RBK1 |
| YCR037c | PHO87 |
| YCR038c | BUD5 |
| YCR039c | MATALPHA2 |
| YCR040w | MATALPHA1 |
| YCR041w | |
| YCR042c | TSM1 |
| YCR043c | |
| YCR044c | |
| YCR045c | |
| YCR046c | IMG1 |
| YCR047c | |
| YCR048w | ARE1 |
| YCR051w | |
| YCR052w | RSC6 |
| YCR053w | THR4 |
| YCR054c | CTR86 |
| YCR057c | PWP2 |
| YCR059c | |
| YCR060w | |
| YCR061W | |
| YCR063w | |
| YCR064c | |
| YCR065w | HCM1 |
| YCR066w | RAD18 |
| YCR067c | SED4 |
| YCR068w | |
| YCR069w | SCC3 |
| YCR071c | IMG2 |
| YCR072c | |
| YCR073c | SSK22 |
| YCR073wa | SOL2 |
| YCR075c | ERS1 |
| YCR076c | |
| YCR077c | PAT1 |
| YCR079w | |
| YCR081w | SRB8 |
| YCR082w | |
| YCR083w | |
| YCR084c | TUP1 |
| YCR085w | |
| YCR086w | |
| YCR087w | |
| YCR088w | ABP1 |
| YCR089w | FIG2 |
| YCR090c | |
| YCR091w | KIN82 |
| YCR092c | MSH3 |
| YCR093w | CDC39 |
| YCR094w | CDC50 |
| YCR095c | |
| YCR096c | A2 |
| YCR097w | A1 |
| YCR098c | GIT1 |
| YCR099c | |
| YCR100c | |
| YCR101c | |
| YCR102c | |
| YCR102wa | |
| YCR103 | |
| YCR104w | PAU3 |
| YCR105w | |
| YCR106w | |
| YCR107w | AAD3 |

Example 2
Genome-Wide Location and Function of DNA-Binding Proteins

Global Analysis of Gal4 Binding Sites

To investigate the accuracy of the genome-wide location analysis method, the analysis was used to identify sites bound by the transcriptional activator Gal4 in the yeast genome. Gal4 was selected because it is among the best characterized transcriptional activators, it is known to be responsible for induction of 10 genes necessary for galactose metabolism, and a consensus DNA binding sequence (the $UAS_G$) has been identified for Gal4 in the promoters of the GAL genes. Very little Gal4 is bound at the $UAS_G$ of the GAL1 and GAL10 promoters when cells are grown in glucose (the repressed state), whereas relatively high levels of Gal4 are bound in galactose (the activated state).

The genome-wide location of epitope-tagged Gal4p in both glucose and galactose media was investigated in three independent experiments, as described in more detail below. The location analysis experiment identified seven genes previously reported to be regulated by Gal4 and three additional genes encoding activities that are physiologically relevant to cells that utilize galactose as the sole carbon source, but which were not previously known to be regulated by this activator (FIGS. 6A).

Figure 6B:
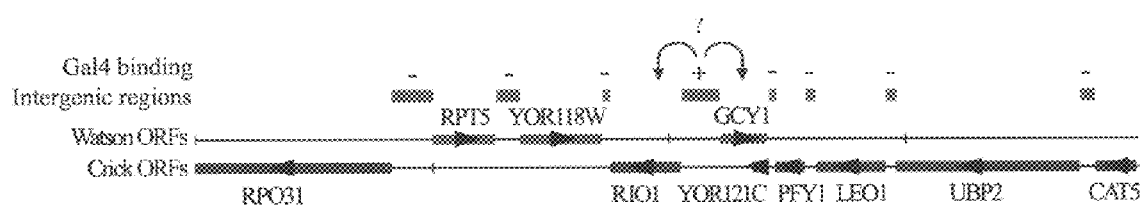
FIG. 6B is a schematic of the Gal4 binding intergenic regions.

The set of 24 genes whose promoter regions are most likely to be bound by Gal4 by the analysis criteria (p-value <0.00001) described herein, is listed in FIG. 6A. Gal4 does not functionally activate all of these genes, however, since only a subset of the genes that share intergenic regions bound by Gal4 will be regulated by this activator (FIG. 6B). To identify genes that are both bound by Gal4 and activated by galactose, genome-wide expression analysis was carried out. The upper panel of FIG. 6A shows genes whose expression is induced in galactose, whereas the lower panel shows genes whose expression is galactose independent. Seven genes previously reported to be regulated by Gal4 (GAL1, GAL2, GAL3, GAL7, GAL10, GAL80 and GCY1) bound Gal4 and were activated in galactose. Three genes whose expression was not previously associated with the Gal4 activator, MTH, PCL10 and FUR4, were also found to be bound by Gal4 and activated in galactose. Substantially less Gal4 was associated with each of these promoters in cells grown in glucose, as expected. Gal4p was not bound to the promoters of GAL4 and PGM2, genes previously thought to be regulated by Gal4, although direct evidence for Gal4 binding to these promoters had not been demonstrated. Each of these results was confirmed by conventional ChIP analysis (FIG. 6C), demonstrating that the microarray results accurately reflect results obtained by the conventional approach, which has until now been used to study binding sites individually.

Figure 6C:
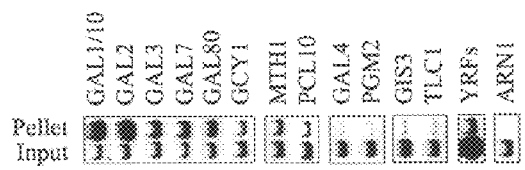
FIG. 6C shows the results of conventional ChIP analysis.
Figure 6D:
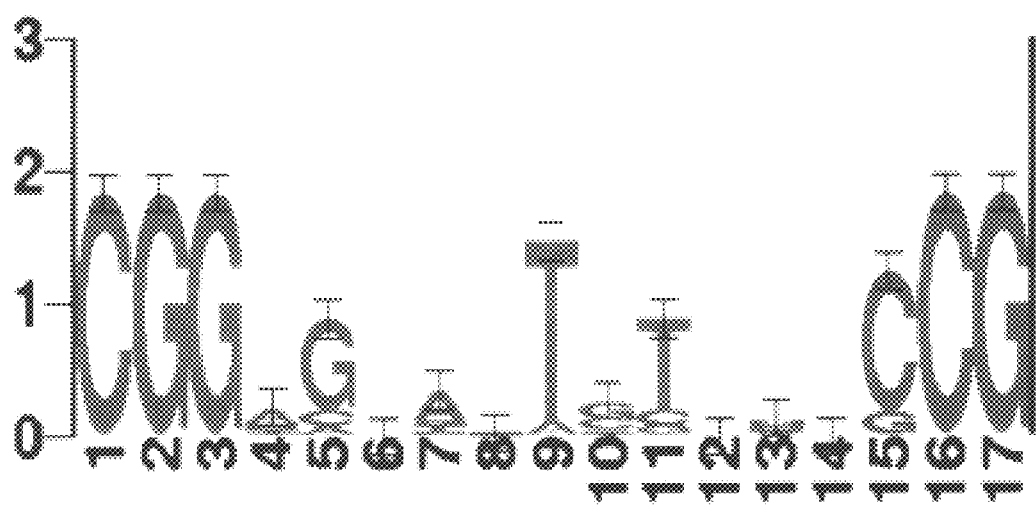
FIG. 6D shows the results of the AlignAce program used to identify a consensus binding site for the Gal4 activator.
Figure 6E:
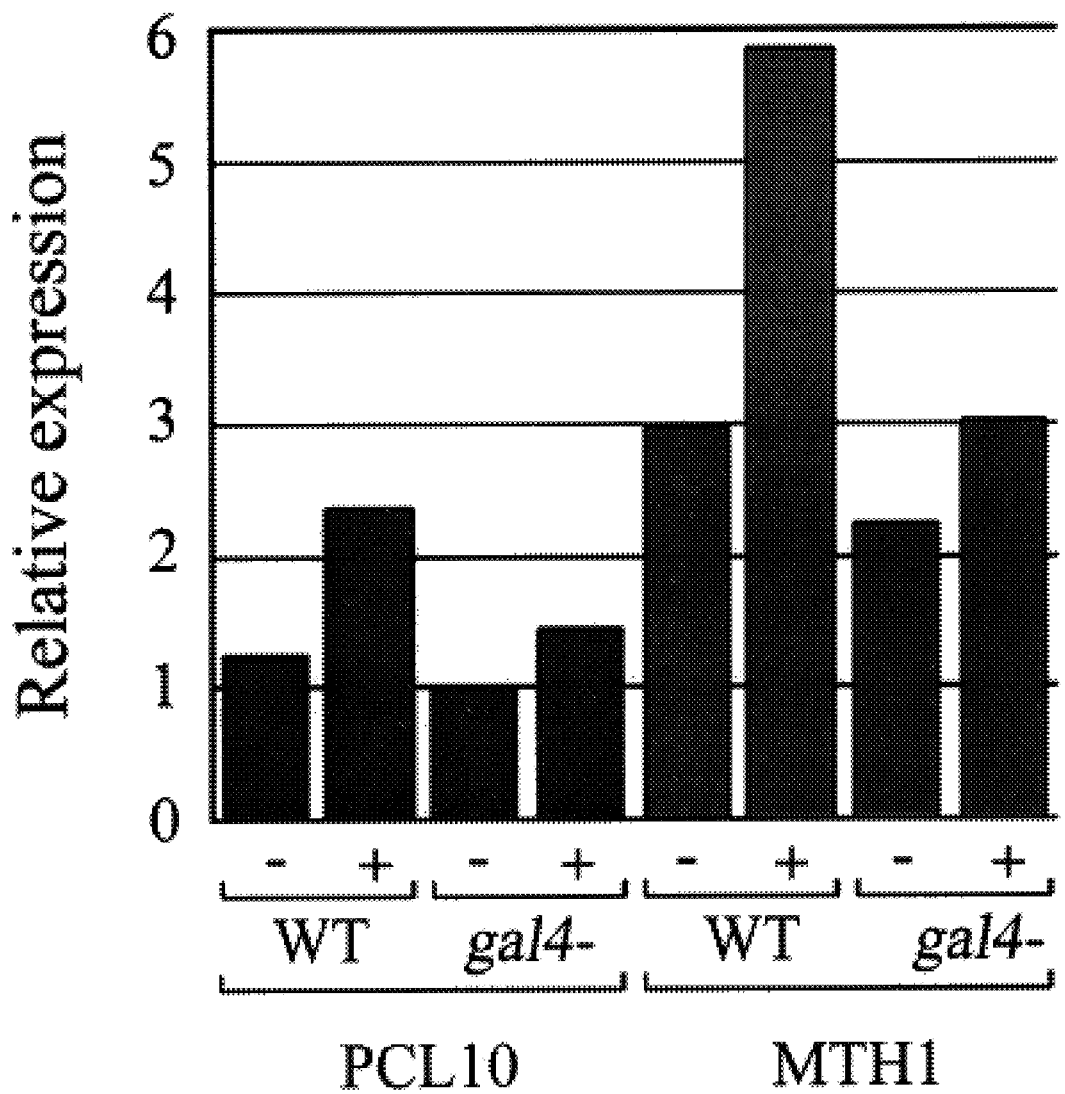
FIG. 6E is a bar graph showing relative expression of PLC10 and MTH1.

The ten genes that are both bound and regulated by Gal4 were selected and the AlignAce program was used to identify a consensus binding site for this activator (FIG. 6D). This binding site sequence is similar to, but refines, the sequence previously determined for Gal4. The Gal4 binding sequence occurs at approximately 50 sites through the yeast genome where Gal4 binding is not detected, indicating that the simple presence of this sequence is not sufficient for Gal4 binding.

Three genes whose expression was not previously associated with the Gal4 activator, MTH, PCL10 and FUR4, were found to be bound by Gal4 and activated in galactose. It is likely that these three genes are genuine Gal4p targets because they share the following three features with the well established Gal4-dependent GAL genes. MTH, PCL10 and FUR4 are galactose-induced (FIG. 6A). Galactose induction depends on Gal4 (FIG. 6C). MTH, PCL10 and FUR4 promoters are bound by Gal4 when cells are grown in galactose but not in glucose (FIG. 6A). The binding of Gal4p to the MTH, PCL10 and FUR4 promoters was verified by conventional ChIP analysis (FIG. 6C).

Figure 6F:
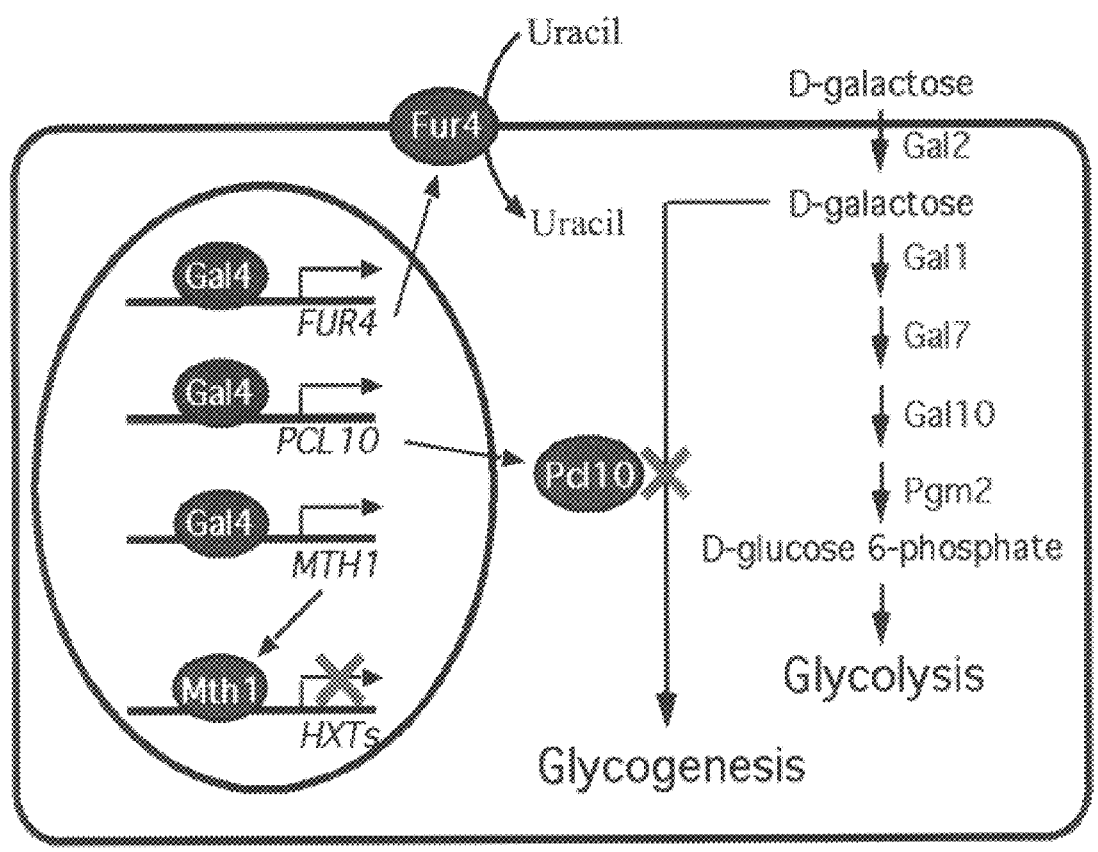
FIG. 6F is a schematic illustrating how the identification of MTH1 and MTH, PCL10 and FUR4 as Gal4-regulated genes reveals how several different metabolic pathways are interconnected.

The identification of MTH1 and MTH, PCL10 and FUR4 as Gal4-regulated genes reveals how regulation of several different metabolic pathways are interconnected (FIG. 6F). MTH1 encodes a transcriptional repressor of many genes involved in metabolic pathways that would be unnecessary when cells utilize galactose as a sole carbon source. Among the most interesting of its targets are a subset of the HTX genes involved in hexose transport. The results described herein indicate that the cell responds to galactose by modifying the concentration of its hexose transporters at the membrane in a Gal4-dependent fashion; Gal4 activates the galactose transporter gene GAL2 and, by activation of MTH1 repressor, causes reduced levels of glucose transporter expression. The Pc110 cyclin associates with Pho85p and appears to repress the formation of glycogen. The observation that PCL10 is Gal4-activated indicates that reduced glycogenesis occurs to maximize the energy obtained from galactose metabolism. FUR4 encodes a uracil pennease and its induction by Gal4 may reflect a need to increase intracellular pools of uracil to permit efficient UDP addition to galactose catalyzed by Gal7.

Previous studies have shown that Gal4 binds to at least some GAL gene promoters when cells are grown on carbon sources other than galactose, as long as glucose is absent. Genome-wide location analysis of Gal4 in cells grown on raffinose was repeated and it was found that the results were essentially identical to those obtained when cells were grown on galactose. These results indicate that Gal4 exhibits the same binding behavior at all its genomic binding sites and demonstrate that the genome-wide location method is highly reproducible.

Global Analysis of Ste12 Binding Sites

The genome-wide binding profile of the DNA-binding transcription activator Ste12 was also investigated. Ste12 is of interest because it has a defined cellular role—it is key to the response of haploid yeast to mating pheromones—but only a few genes regulated by Ste12 have been identified. Activation of the pheromone-response pathway causes cell cycle arrest and transcriptional activation of more than 100 genes. Expression analysis using ste12 mutant cells has shown that Ste12 is required for the pheromone induction of all of these genes. However, the mechanism by which Ste12 activates transcription of these genes in response to pheromone has not been elucidated.

Figure 7A:
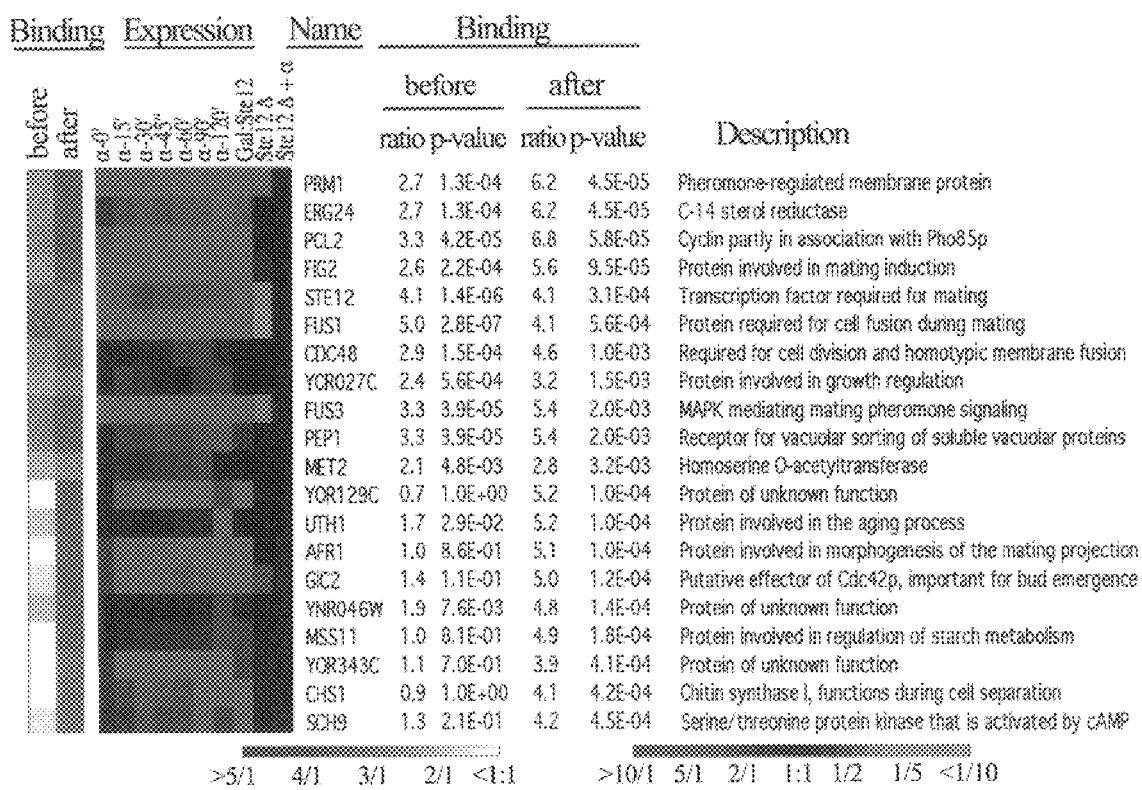
FIG. 7 lists the set of genes whose promoter regions are most likely to be bound by Ste112 by the analysis criteria described herein.
Figure 7B:
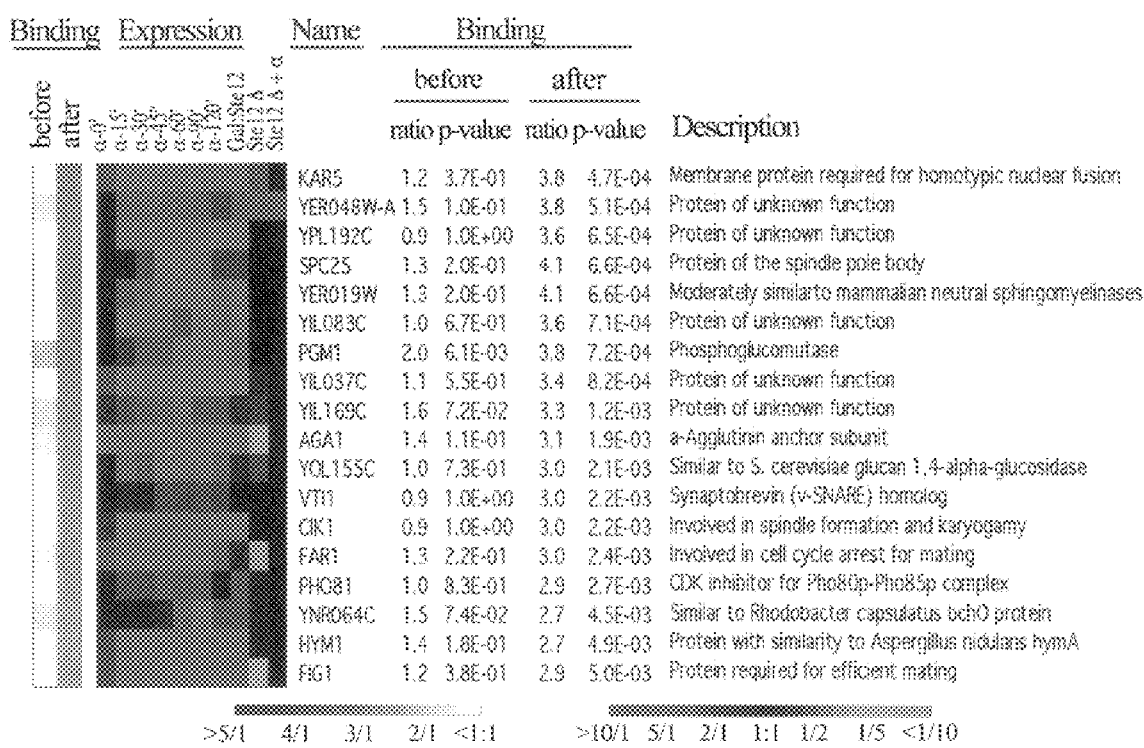
Figure 7C:
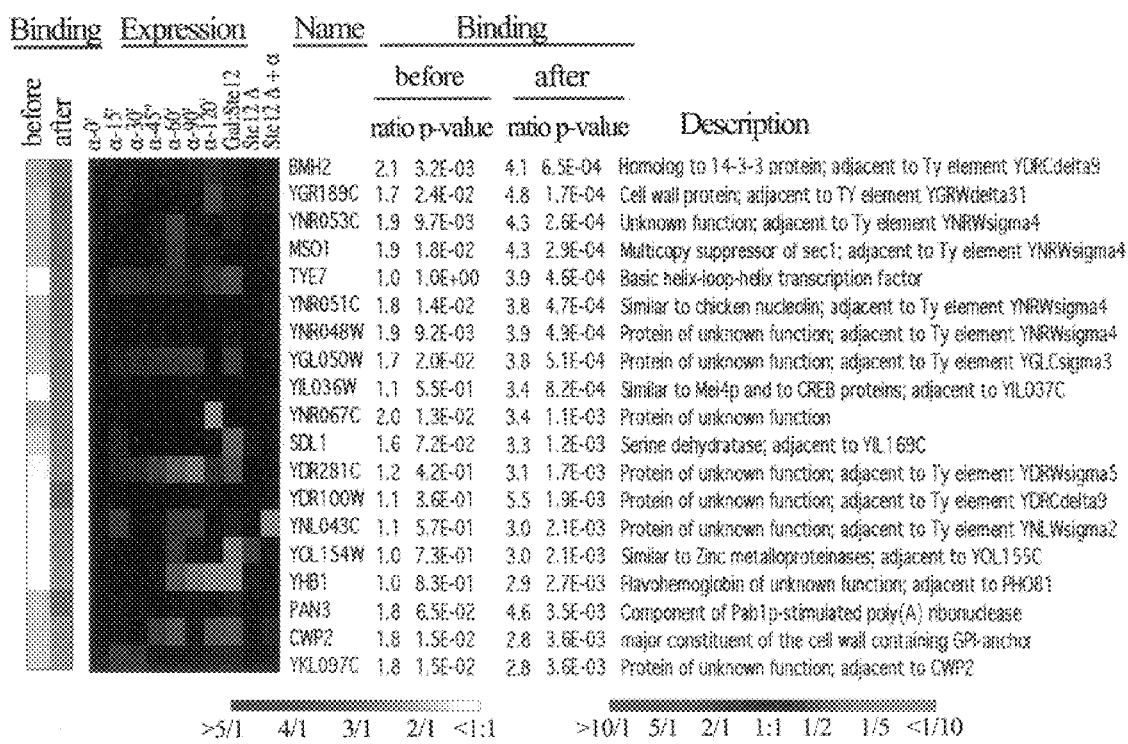

The genome-wide location of epitope-tagged Ste12p before and after pheromone treatment was investigated in three independent experiments. The set of genes whose promoter regions are most likely to be bound by Ste 12 by the analysis criteria (p-value <0.005) described herein is listed in FIG. 7; the upper panel shows genes whose expression is induced by alpha factor, whereas the lower panel shows genes whose expression is not significantly induced by alpha factor. Of the 36 genes that are induced by alpha factor and are bound by Ste12, 12 are known to participate in various steps of the mating process (FIG2, AFR1, GIC2, STE12, CHS1, KAR5, FUS1, AGA1, FUS3, CIK1, FAR1, FIG1).

Ste12 binds to some promoters in the absence of pheromone signaling, however, its binding to most genes is enhanced by alpha factor. Interestingly, Ste12p is bound to its own promoter both before and after pheromone treatment. Together, the binding and expression data argue that the regulation of the STE12 gene involves a positive feedback loop. STE12 expression is increased immediately after pheromone treatment, indicating that the bound but inactive Ste12 activator is rapidly converted to an active form. Increased expression of STE12 gene would allow more Ste12p to be made and this would, in turn, activate its genes.

Twenty-four genes whose expression were not previously associated with Ste12 and the mating process were found to be bound by Ste12 and activated by alpha factor. Considering that their pheromone induction is eliminated in ste12 mutant cells, it is likely that these 24 genes are also genuine Ste12 targets. The identities of these genes indicate interesting details about various steps of the mating process. For example, one Ste12 target gene, PCL2, encodes a G1 cyclin that forms complexes with the cyclin—dependent kinase (cdk) Pho85. The Pc12-Pho85 and PC11-Pho85 complexes act in concert with Cln1-Cdc28 and Cln-2-Cdc28 cyclin dependent kinase complexes to promote G1cell cycle progression (Measday et al., 1994). The Pc12-Pho85 kinase complex has a substrate specificity that is overlapping but different from that of the Cln1-Cdc28 and Cln2-Cdc28. During the mating process, haploid yeast cells are arrested at start of the late G1 phase, due to the inhibition of Cln1-Cdc28 and Cln2-Cdc28 activities by Far1, which is encoded by another Ste12 target gene. Activation of PCL2 by Ste12 after pheromone treatment indicates that increased Pho85 complex activities are likely necessary to compensate for the loss of Cdc28 activities.

Most Ste12 target genes identified by analysis of genome locations of Ste12 and expression profiles during pheromone induction encode proteins involved in various steps of the mating response. Among them are 11 previously uncharacterized. The cellular roles for these genes, including YNL279W, YOR129C, YOR343C, YPL192C, YER019W, YIL083C, YIL037C, YIL169C, YNL105W, YOL155C and YNR064C, are therefore most likely related to mating.

Ste12 has also been implicated in other cellular processes. Together with Tec1, Ste12 regulates the filmamentation of diploid cells and invasive growth in haploids. Two genes, TEC1 and FLO11, have been identified as Ste12 targets in filamentous growth pathway. Ste12 binding to these genes either in the presence or absence of alpha factor was not detected. It is likely that Ste12p's binding to these promoters is regulated by different physiological conditions.

What is claimed is:

1. A method of identifying a region of a genome of a living cell to which a protein of interest binds, comprising the steps of:
   a) crosslinking DNA binding protein in the living cell to genomic DNA of the living cell, thereby producing DNA binding protein crosslinked to genomic DNA;
   b) generating DNA fragments of the genomic DNA crosslinked to DNA binding protein in a), thereby producing a mixture comprising DNA fragments to which DNA binding protein is bound;
   c) removing a DNA fragment to which the protein of interest is bound from the mixture produced in b);
   d) separating the DNA fragment identified in c) from the protein of interest;
   e) amplifying the DNA fragment of d);
   f) combining the DNA fragment of e) with DNA comprising a sequence complementary to genomic DNA of the cell, under conditions in which hybridization between the DNA fragment and a region of the sequence complementary to genomic DNA occurs; and g) identifying the region of the sequence complementary to genomic DNA of f) to which the DNA fragment hybridzes, whereby the region identified in g) is the region of the genome in the cell to which the protein of interest binds.

2. The method of claim 1 wherein the cell is a eukaryotic cell.

3. The method of claim 1 wherein the protein of interest is selected from the group consisting of: a transcription factor and an oncogene.

4. The method of claim 1 wherein the DNA binding protein of the cell is crosslinked to the genome of the cell using formaldehyde.

5. The method of claim 1 wherein the DNA fragment of c) to which is bound the protein of interest is identified using an antibody which binds to the protein of interest.

6. The method of claim 1 wherein the DNA fragment of e) is amplified using ligation-mediated polymerase chain reaction.

7. The method of claim 1 wherein the complement sequence of the genome of f) is a DNA microarray.

8. The method of claim 1 further comprising:

h) comparing the region identified in g) with a control.

9. A method of identifying a region of a genome of a living cell to which a protein of interest binds, comprising the steps of:

a) formaldehyde crosslinking DNA binding protein in the living cell to genomic DNA of the living cell, thereby producing DNA binding protein crosslinked to genomic DNA;

b) generating DNA fragments of the genomic DNA crosslinked to DNA binding protein in a), thereby producing DNA fragments to which DNA binding protein is bound;

c) immunoprecipitating the DNA fragment produced in b) to which the protein of interest is bound using an antibody that specifically binds the protein of interest;

d) separating the DNA fragment identified in c) from the protein of interest;

e) amplifying the DNA fragment of d) using ligation-mediated polymerase chain reaction;

f) fluorescently labeling the DNA fragment of e);

g) combining the labeled DNA fragment of e) with a DNA microarray comprising a sequence complementary to genomic DNA of the cell, under conditions in which hybridization between the DNA fragment and a region of the sequence complementary to genomic DNA occurs;

h) identifying the region of the sequence complementary to genomic DNA to which the DNA fragment hybridizes by measuring the fluorescence intensity; and i) comparing the fluorescence intensity measured in h) to the fluorescence intensity of a control, whereby fluorescence intensity in a region of the genome which is greater than the fluorescence intensity of the control in the region indicates the region of the genome in the cell to which the protein of interest binds.

10. A method of determining a function of a protein of interest which binds to a genome of a living cell, comprising the steps of:

a) crosslinking DNA binding protein in the living cell to genomic DNA of the living cell, thereby producing DNA binding protein crosslinked to genomic DNA;

b) generating DNA fragments of the genomic DNA crosslinked to DNA binding protein in a), thereby producing a mixture comprising DNA fragments to which DNA binding protein is bound;

c) removing the DNA fragment to which the protein of interest is bound from the mixture produced in b);

d) separating the DNA fragment identified in c) from the protein of interest;

e) amplifying the DNA fragment of d);

f) combining the DNA fragment of e) with DNA comprising a sequence complementary to genomic DNA of the cell, under conditions in which hybridization between the DNA fragment and a region of the sequence complementary to genomic DNA occurs;

g) identifying the region of the sequence complementary to genomic DNA of f) to which the DNA fragment hybridzes; and h) characterizing the region identified in g), wherein the characteristics of the region of h) indicates a function of the protein of interest which binds to the genome of the cell.

11. A method of determining whether a protein of interest which binds to the genome of a living cell functions as a transcription factor, comprising the steps of:

a) crosslinking DNA binding protein in the living cell to the genomic DNA of the living cell, thereby producing DNA binding protein crosslinked to genomic DNA;

b) generating DNA fragments of the genomic DNA crosslinked to DNA binding protein in a), thereby producing a mixture comprising DNA fragments to which DNA binding protein is bound;

c) removing the DNA fragment to which the protein of interest is bound from the mixture produced in b);

d) separating the DNA fragment identified in c) from the protein of interest;

e) amplifying the DNA fragment of d);

f) combining the DNA fragment of e) with DNA comprising a sequence complementary to genomic DNA of the cell, under conditions in which hybridization between the DNA fragment and a region of the sequence complementary to genomic DNA occurs; and g) identifying the region of the sequence complementary to genomic DNA of f) to which the DNA fragment hybridzes, wherein if the region of the sequence complementary to genomic DNA of g) is a regulatory region, then the protein of interest is a transcription factor.

* * * * *